(12) United States Patent
Scheule

(10) Patent No.: US 10,966,697 B2
(45) Date of Patent: Apr. 6, 2021

(54) VASCULAR CLOSURE DEVICE AND METHOD OF POSITIONING VASCULAR CLOSURE DEVICE

(71) Applicant: CaveoMed GmbH, Tübingen (DE)

(72) Inventor: Albertus M. Scheule, Tübingen (DE)

(73) Assignee: CaveoMed GmbH

( * ) Notice: Subject to any disclaimer, the term of this patent is extended or adjusted under 35 U.S.C. 154(b) by 415 days.

(21) Appl. No.: 15/203,491

(22) Filed: Jul. 6, 2016

(65) Prior Publication Data

US 2016/0310118 A1  Oct. 27, 2016

Related U.S. Application Data

(63) Continuation-in-part of application No. 14/889,053, filed as application No. PCT/EP2014/058645 on Apr. 29, 2014, now Pat. No. 10,716,550.

(30) Foreign Application Priority Data

May 6, 2013 (EP) ..................... 13166631

(51) Int. Cl.
*A61B 17/00* (2006.01)
*A61B 17/22* (2006.01)
*A61B 90/00* (2016.01)

(52) U.S. Cl.
CPC ............... *A61B 17/0057* (2013.01); *A61B 2017/00637* (2013.01); *A61B 2017/00676* (2013.01);
(Continued)

(58) Field of Classification Search
CPC ...... A61B 17/0057; A61B 2017/00637; A61B 2017/00676; A61B 2017/00884;
(Continued)

(56) References Cited

U.S. PATENT DOCUMENTS 5,279,546 A * 1/1994 Mische ............ A61B 17/22012
604/101.03
6,071,300 A 6/2000 Brenneman et al.
(Continued)

FOREIGN PATENT DOCUMENTS

CN 201578302 9/2010
JP 2006/516445 7/2006
(Continued)

*Primary Examiner* — Kathleen S Holwerda
*Assistant Examiner* — Brooke Labranche
(74) *Attorney, Agent, or Firm* — Pandiscio & Pandiscio

(57) ABSTRACT

The present invention relates to a vascular closure device for sealing a puncture site in a vascular wall comprising a sheath (10) having a distal end and at least one proximal end, wherein the sheath (10) comprises a tubular body (100). The vascular closure device (1) is characterized in that at least one distal balloon member (11) is firmly arranged at the distal end of the tubular body (100) of the sheath (10) and at least one expandable anchor member (12) is firmly arranged proximal to the distal balloon member (11) on the tubular body of the sheath (10), wherein at least the distal side of the distal balloon member (11) is a pressure area for applying pressure on the outside of the vascular wall. Furthermore a method of positioning of a vascular closure device (1) is described.

21 Claims, 8 Drawing Sheets

(52) U.S. Cl.
CPC ............... *A61B 2017/00884* (2013.01); *A61B 2017/22054* (2013.01); *A61B 2017/22067* (2013.01); *A61B 2017/22069* (2013.01); *A61B 2090/034* (2016.02)

(58) Field of Classification Search
CPC ........... A61B 2017/22054; A61B 2017/22067; A61B 2017/22069; A61B 2090/034
See application file for complete search history.

(56) References Cited

U.S. PATENT DOCUMENTS

| | | | |
|---|---|---|---|
| 6,595,953 B1* | 7/2003 | Coppi | A61B 17/12045 |
| | | | 604/93.01 |
| 6,733,515 B1* | 5/2004 | Edwards | A61B 17/00491 |
| | | | 604/264 |
| 8,636,724 B2 | 1/2014 | Wiita et al. | |
| 2003/0023204 A1* | 1/2003 | Vo | A61B 17/22 |
| | | | 604/103.07 |
| 2003/0149463 A1 | 8/2003 | Solymar et al. | |
| 2009/0062836 A1 | 3/2009 | Kurrus | |
| 2012/0065637 A1 | 3/2012 | Lindenbaum et al. | |
| 2013/0096499 A1 | 4/2013 | Tchirikov | |
| 2014/0236222 A1* | 8/2014 | Tegels | A61B 17/0057 |
| | | | 606/213 |
| 2014/0371789 A1* | 12/2014 | Hariton | A61B 17/00234 |
| | | | 606/215 |

FOREIGN PATENT DOCUMENTS

| | | | | |
|---|---|---|---|---|
| JP | 2007/520306 | 7/2007 | | |
| WO | WO 97/09934 | 3/1997 | | |
| WO | WO 99/02091 | 1/1999 | | |
| WO | WO 2004/069300 | 8/2004 | | |
| WO | WO 2004069300 A2 * | 8/2004 | ......... | A61B 17/0057 |
| WO | WO 2009/023866 | 2/2009 | | |
| WO | WO 2010/096530 | 8/2010 | | |

* cited by examiner

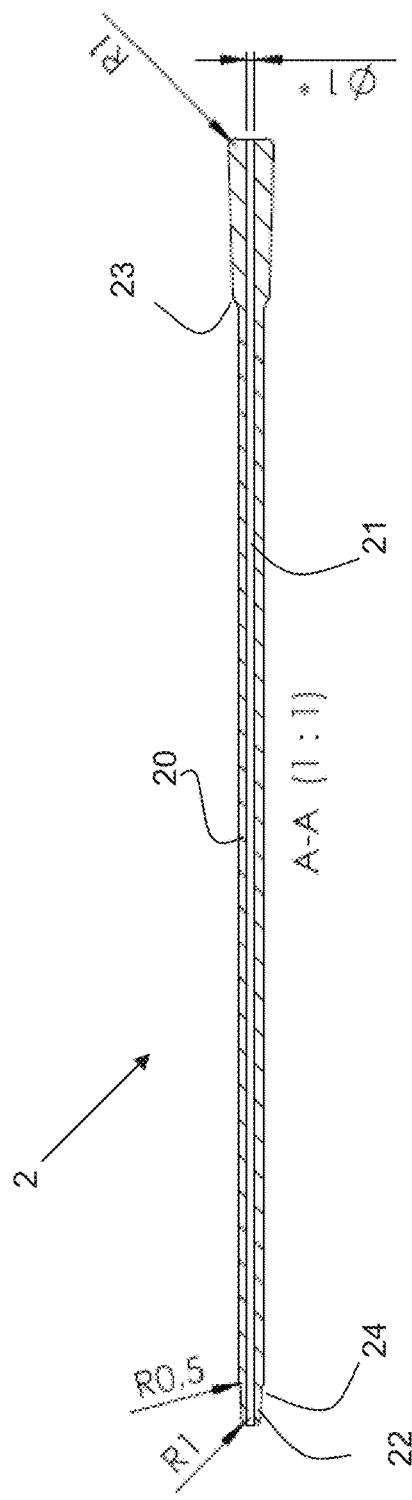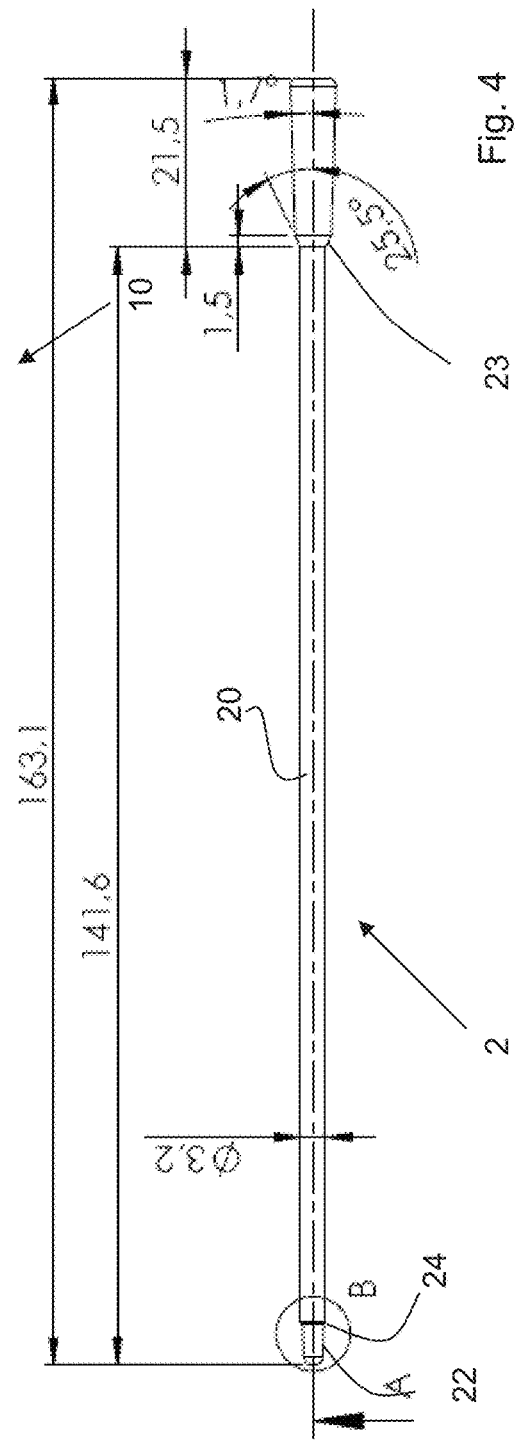

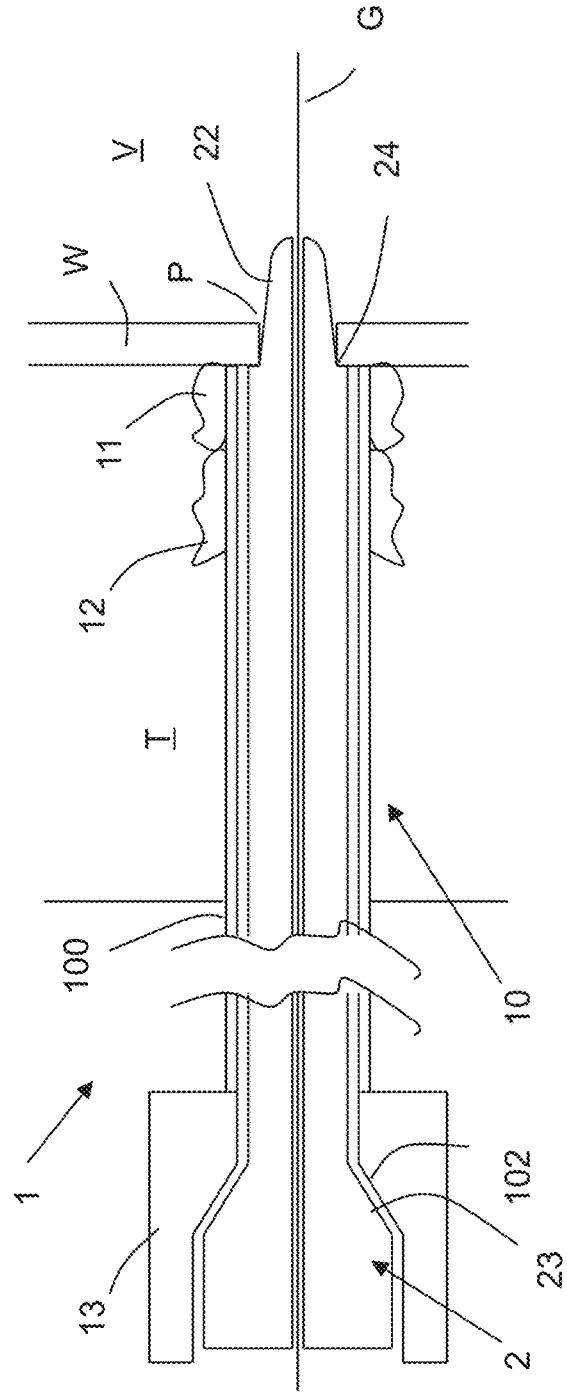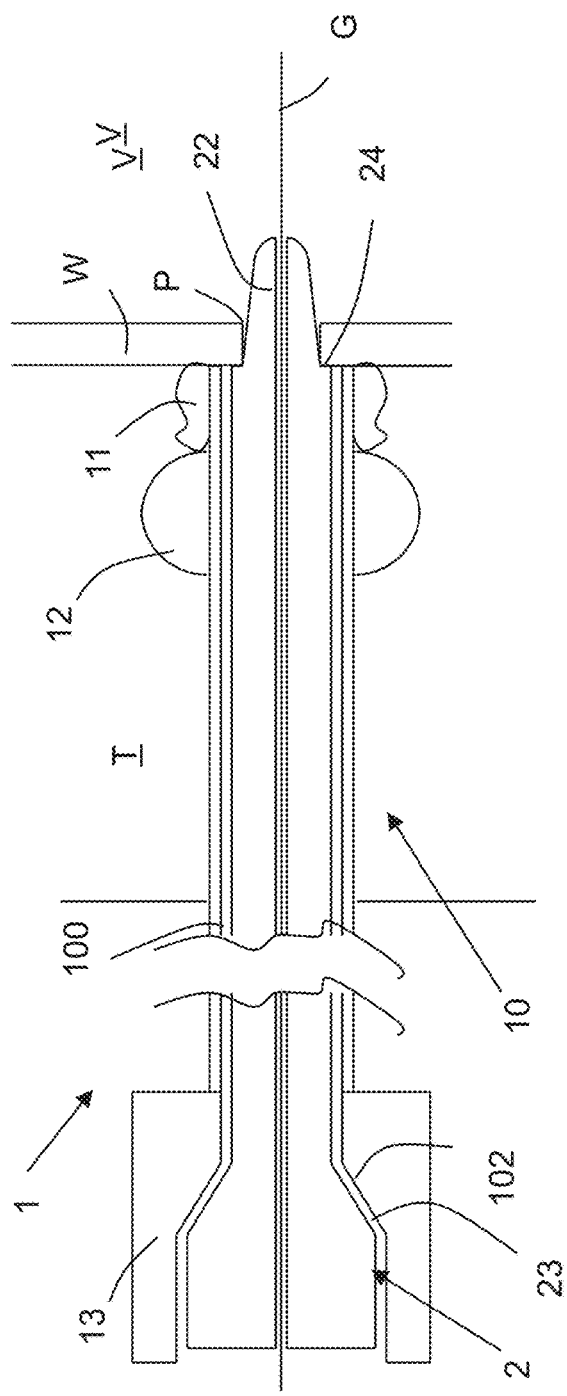

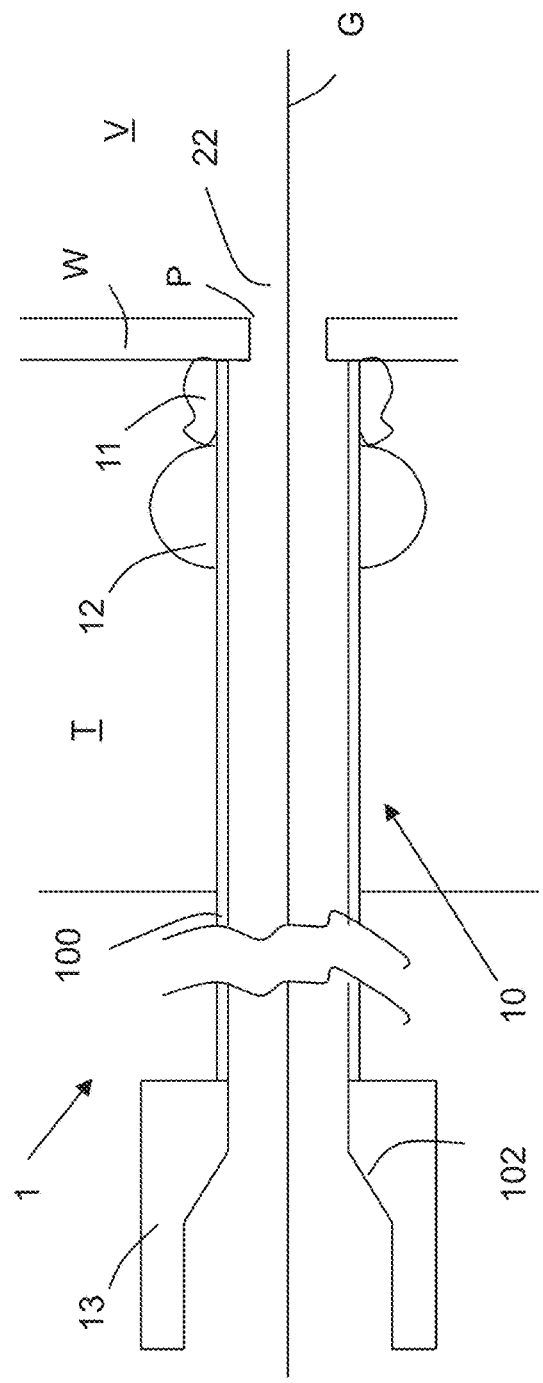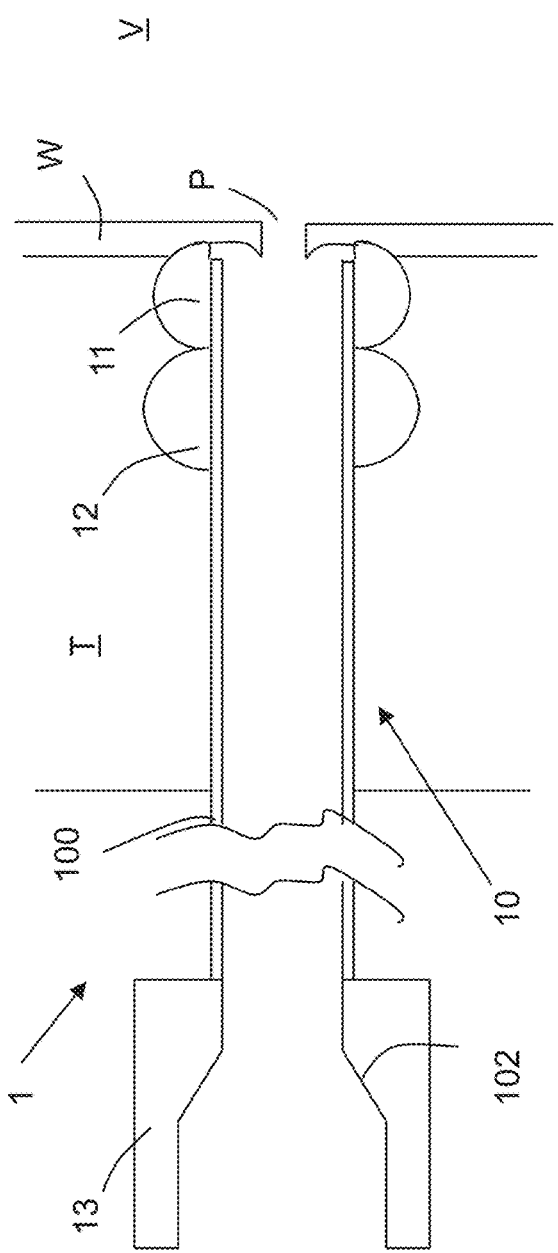

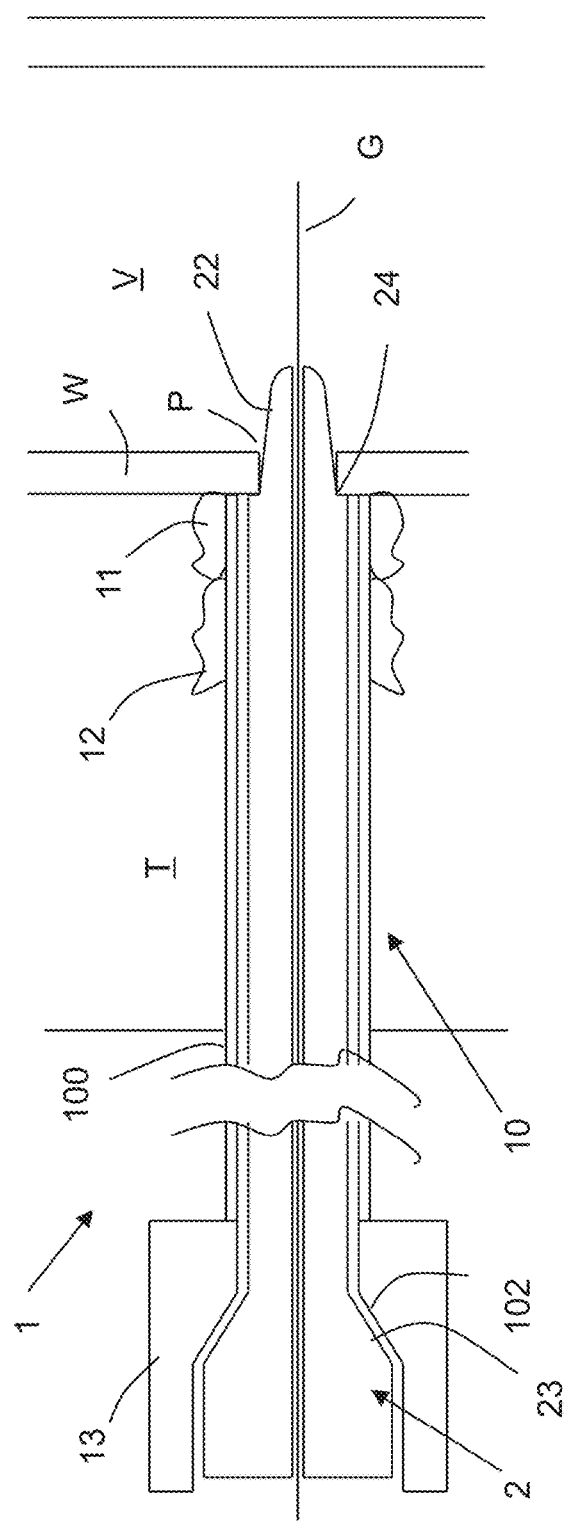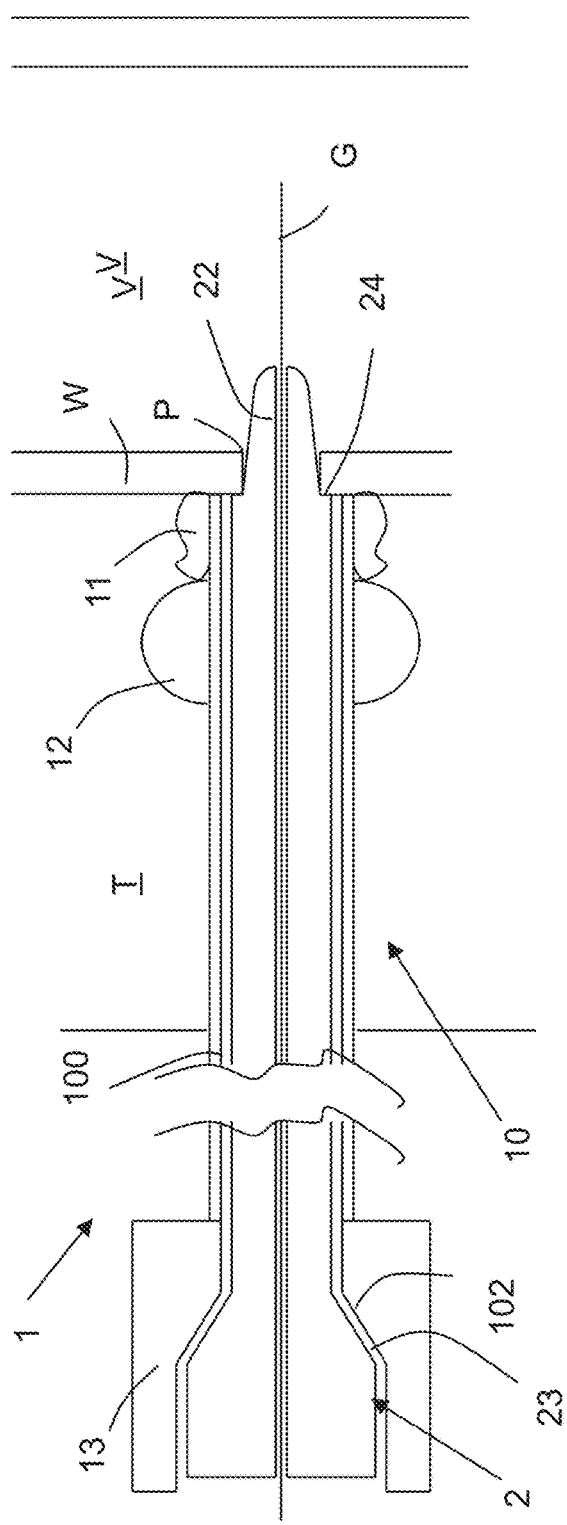

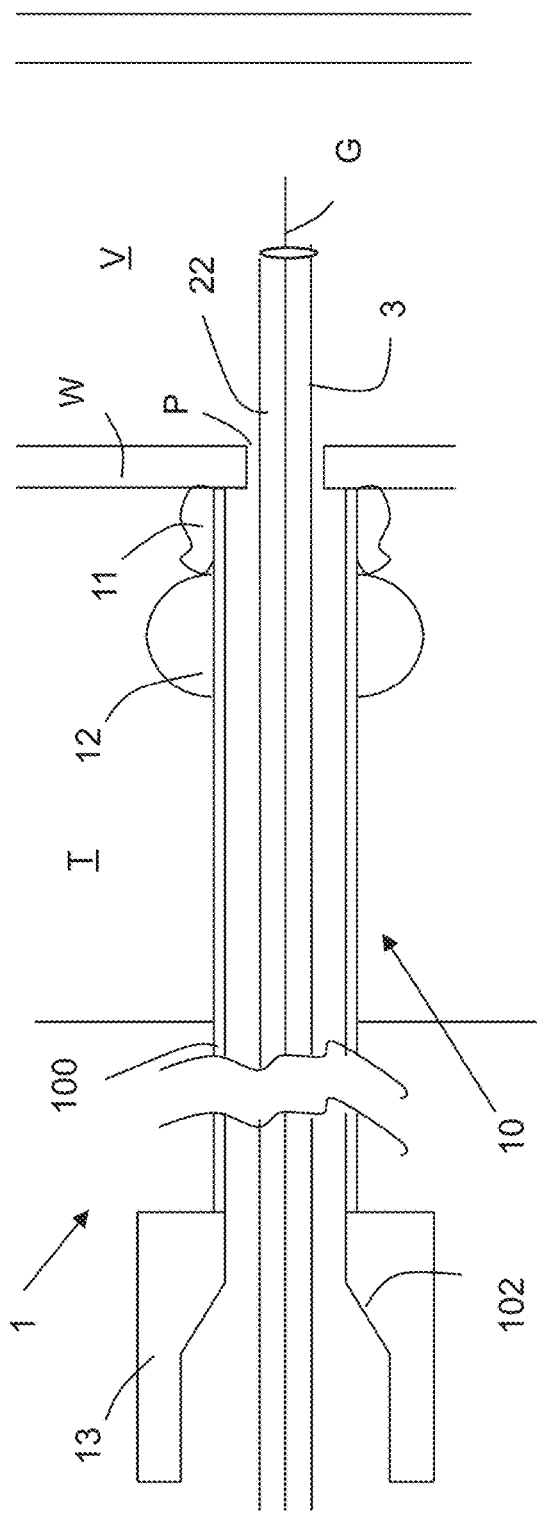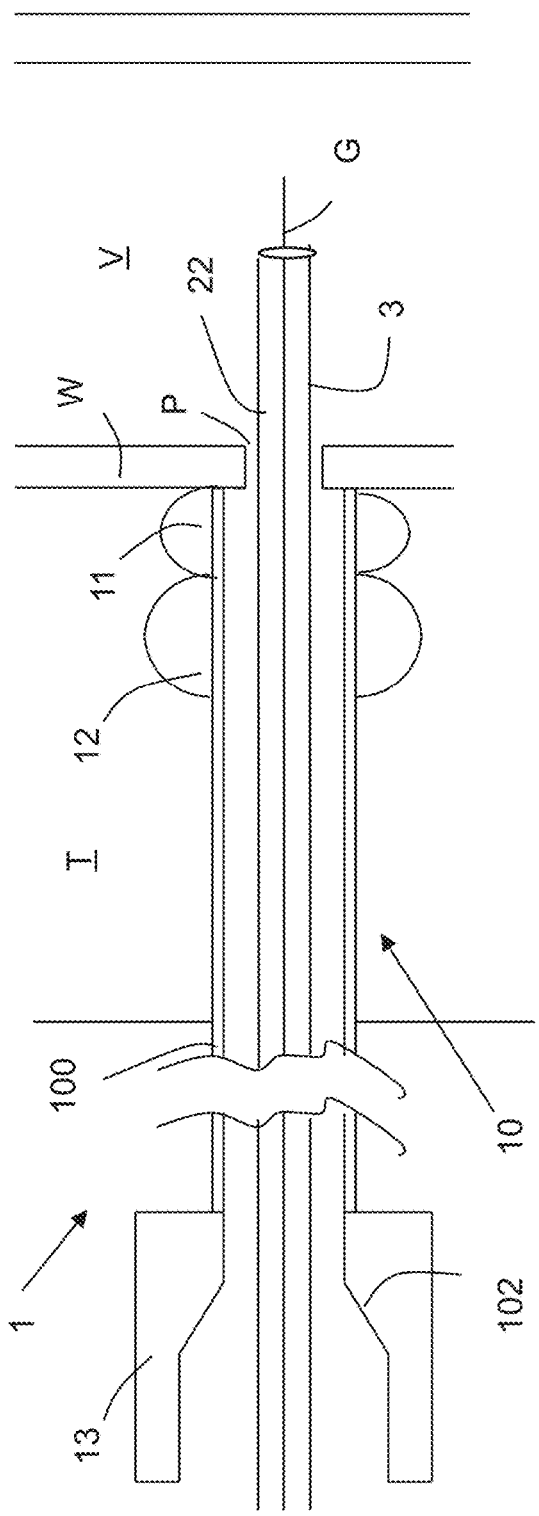

VASCULAR CLOSURE DEVICE AND METHOD OF POSITIONING VASCULAR CLOSURE DEVICE

REFERENCE TO PENDING PRIOR PATENT APPLICATIONS

This patent application is a continuation-in-part of pending prior U.S. patent application Ser. No. 14/889,053, filed Nov. 4, 2015 by CaveoMed GmbH for VASCULAR CLOSURE DEVICE AND METHOD OF POSITIONING VASCULAR CLOSURE DEVICE, which patent application in turn claims benefit of International (PCT) Patent Application No. PCT/EP2014/058645, filed 29 Apr. 2014 by CaveoMed GmbH for VASCULAR CLOSURE DEVICE AND METHOD OF POSITIONING VASCULAR CLOSURE DEVICE, which claims benefit of European Patent Application No. EP 13166631.5, filed 6 May 2013, which patent applications are hereby incorporated herein by reference.

FIELD OF THE INVENTION

The present invention relates to a vascular closure device and a method of positioning a vascular closure device.

BACKGROUND OF THE INVENTION

In endovascular diagnostics and therapy of cardiac and vascular diseases access to the arterial system is generally necessary. Such access may be provided for example via the femoral artery or other vessels. After puncture of the artery, a vascular sleeve or introducer is implanted. The diagnostic or therapeutic catheter may be placed via this vascular sleeve or introducer. After termination of the intervention the sleeve or introducer is removed and percutaneous pressure is applied from the outside of the human body to the puncture site. Thereby, the puncture site can be sealed by compression with aid of the body's own coagulation.

Initially this requires a longer manual compression followed by a compression for several hours by means of an applied bandage. Not only but especially with obese patients, the pressure which can be applied to the puncture site is not sufficiently focused, so that increased bleeding into the perivascular tissue may occur. Such haematomas are threatening for the patient.

Vascular closure devices have been suggested which apply pressure to the puncture site from within the body. For example in WO 2010/096530 a tissue puncture closure device is described. In this tissue puncture closure device an anchor means is inserted into the blood vessel and a plug is provided on the outside of the vessel in the tissue. One disadvantage of this known device is that its design and thus manufacturing and handling is rather complex. In addition, the remaining of parts, in particular the plug, within the tissue requires use of material which is biodegradable. Furthermore the device may not be used with patients with allergic reactions to the materials used, in particular as the components of the device partially remain in the body.

The problem to be solved with the present invention is thus to provide a vascular closure device and positioning method which at least partially overcome these drawbacks. In particular, a solution should be provided, which allows for reliable and fast sealing of a puncture site in a vessel wall with minimal impact on the patient.

SUMMARY OF THE INVENTION

The invention is based on the finding, that this problem can be solved by providing a device, wherein an anchor element for fixing the position and a pressure element for providing pressure onto the puncture site are suitably provided on a single component of the vascular closure device which can be removed from the puncture site, thereby also removing the anchor element and the pressure element.

According to a first aspect, the invention relates to a vascular closure device for sealing a puncture site in a vascular wall. The vascular closure device comprises a sheath having a distal end and at least one proximal end and the sheath comprises a tubular body. The vascular closure device is characterized in that at least one distal balloon member is firmly arranged at the distal end of the tubular body of the sheath and at least one expandable anchor member is firmly arranged proximal to the at least one distal balloon member on the tubular body of the sheath, wherein at least the distal side of the distal balloon member is a pressure area for applying pressure onto the outside of the vascular wall.

A vascular closure device according to the present invention is a medical device which is at least partially inserted into the tissue of a human body. The insertion into the tissue of a human body according to the invention is temporary, that means the part of the vascular closure device which has been inserted into the tissue will be removed after termination of the treatment process.

The vascular closure device according to the invention serves for sealing a puncture site in a vascular wall. Sealing of the puncture site according to the invention refers to applying pressure onto the puncture site, thereby closing the puncture site. The closure of the puncture site may be effected by the vascular closure device directly or may be promoted by the vascular closure device. In particular, coagulation of blood at the puncture site, which leads to closing the puncture site may be promoted by the vascular closure device in addition to, or alternatively to applying pressure onto the puncture site.

The vascular wall, where the puncture to be sealed is entered preferably is a vessel wall of an arteria. The arteria or artery may also be referred to as arterial vessel. The invention is not limited to the use at an artery but may also be used at other blood vessels. Hence, hereinafter reference is made to blood vessels or vessels. For example, the puncture may be provided in the femoral artery or other vessels.

The vascular closure device according to the invention comprises a sheath having a distal end and at least one proximal end. The sheath comprises a tubular body portion and may also be referred to as a catheter or sleeve. The sheath according to the invention is thus hollow, that means has at least one lumen, and other medical devices may be inserted into or may be introduced through the sheath. The sheath has a distal end and at least one proximal end. If more than one proximal end is provided, the branching of the proximal ends may be incorporated in the tubular body of the sheath or may be provided by a hub, which is attached to the tubular body.

At least the distal area of the sheath is formed by the tubular body of the sheath. Hereinafter therefore reference made to the part of the sheath in the distal area is to be understood as reference to the tubular body.

At least the distal end of the sheath, in particular the distal end of the tubular body, is inserted into the tissue of the human body. The proximal end(s) of the sheath, however, remain outside of the body of the patient. The length of the sheath and in particular of the tubular body is thus chosen to be greater than the distance of the vascular wall with the puncture from the skin.

The distal end of the sheath and thus the distal end of the tubular body is the end which is remote to the user and which is inserted into the body, in particular into the tissue.

The proximal end(s) of the sheath denote the end(s) which face towards the user, in particular the physician performing the treatment.

A distal balloon member is firmly arranged at the distal end of the tubular body of the sheath. The distal balloon member is preferably arranged on the outside of the tubular body of the sheath and may be expanded in a radial direction of the sheath. In addition, the distal balloon member may extend beyond the distal end of the tubular body of the sheath at least in an expanded or inflated state of the balloon member. Being arranged at the distal end of the tubular member of the tubular body of the sheath, according to the present invention is to be understood as being positioned at the distal tip of the tubular body of the sheath or being positioned in the vicinity of the distal tip of the tubular body of the sheath. Most preferably, the distal balloon member comprises flexible material, which is attached to the outside of the tubular body of the sheath and surrounds the entire circumference of the outside of the tubular body at the distal end of the tubular body. Once inflated, the flexible material expands in a radial direction from the outside of the tubular body, that means from the sheath. In addition, the flexible material may expand over the distal end of the tubular body of the sheath and in the proximal direction from its deflated state. The shape of the balloon member after inflation or expansion is preferably the shape of a torus or a torus with a flattened inner side. In the latter case, the outer shape of the balloon member in the inflated state is that of a ball and the ball shape is penetrated and thus interrupted by the tubular body of the sheath. An inflation hole is provided in the tubular member of the sheath in the area of the distal balloon member in order to be able to supply media to the inside of the distal balloon member.

The distal balloon member is firmly arranged on the tubular body. That means that the material forming the balloon is firmly attached to the tubular body of the sheath. That means that the flexible material forming the balloon remains on the tubular body during insertion of the sheath into the tissue and also during removal from the tissue. The flexible material may for example be glued to the outside of the tubular body. The distal balloon member according to the invention may be deflated. In the deflated state of the distal balloon member the sheath of the vascular closure device can be inserted into and retracted from the tissue without hindering the movement of the sheath.

According to the invention, at least one expandable anchor member is firmly arranged proximal to the distal balloon member on the tubular body of the sheath. The expandable anchor member is a member on the sheath that may be expanded at least in a radial direction of the sheath. The anchor member may be a balloon member or for example a mesh member. Preferably, the expandable anchor member is arranged proximally adjacent to the distal balloon member on the tubular body of the sheath. The expandable anchor member is firmly arranged on the tubular body. That means that the material forming the expandable anchor member, for example flexible balloon material or a mesh, is firmly attached to the tubular body of the sheath. That means that the expandable anchor member remains on the tubular body during insertion of the sheath into the tissue and also during removal from the tissue. The expandable anchor member according to the invention may be unexpanded or deflated. In the unexpanded or deflated state of the expandable anchor member the sheath of the vascular closure device can be inserted into and retracted from the tissue without hindering the movement of the sheath.

According to the invention at least the distal side of the distal balloon member is a pressure area for applying pressure on the outside of the vascular wall. The distal side of the distal balloon member is the side, which at least in an inflated state of the distal balloon member is facing in the distal direction. At least the pressure area of the distal balloon member is made of a material suitable for applying pressure to the vascular wall directly or indirectly via tissue. In one embodiment, the pressure area thus covers the entire surface of the distal balloon member.

According to the present invention, the pressure area of the distal balloon member is an area suitable for applying pressure onto the outside of the vascular wall, in particular at the puncture site or in the vicinity of the puncture site. The pressure area of the balloon member thus has to be oriented at least partially in the distal direction and is not to be covered or otherwise hindered by other parts of the vascular closure device. As the distal balloon member according to the invention is arranged at the distal end of the tubular body of the sheath, the distal side, that means the distal half of the ball shape or torus shape can serve as pressure area according to the invention.

In a preferred embodiment, the pressure area may be a contact area for contact with the outside of the vascular wall. In that case, the inflated distal balloon member will be in direct contact with the outside of the vascular wall at the puncture site or in the vicinity of the puncture site.

By providing a vascular closure device which has an expandable anchor member as well as a distal balloon member arranged on the tubular body of the sheath of the device, a number of advantages can be achieved. In particular, the anchor member may serve for securing the position of the vascular closure device in the tissue outside of the vessel wall. Hence, this securing of the position, may be performed at an early stage of the treatment process. In particular the anchor member may be deployed immediately after the distal part of the tubular body of the sheath vascular closure device has been introduced into the tissue. Subsequent intervention steps, such as endovascular diagnostic steps or therapy steps, may thus be performed through the sheath, which is securely held in a position by the anchor member. As in addition also the distal balloon member is provided on the tubular member of the sheath of the vascular closure device the relative position of these two members is fixed. There is, hence, no need for the physician to adjust the relative position of these two members during the intervention. Finally, as the distal balloon member has a pressure area for applying pressure onto the outside of the vessel wall, the closing of a puncture in the vessel wall can be performed with the same vascular closure device which has already been used for guiding the medical instruments used in the intervention. There is no need to introduce a different closure device after termination of the intervention into the tissue which reduces the risks for the patient and also reduces the overall treatment duration. As the distal balloon member and the expandable anchor member are firmly attached to the tubular body of the sheath, these members can be removed in one step together with the tubular body of the sheath at the end of the treatment. This also reduces the treatment time. In addition, no components of the vascular closure device remain in the tissue or blood vessel, so that the usage of the inventive vascular closure device is also more acceptable for the patient and can be used irrespective of potential incompatibility of the patient with the material of the vascular closure device over a longer period of time.

For the treatment of thrombolysis the distal balloon member may also be expanded during the intervention. In particular, the distal balloon member may be expanded after insertion of a treatment catheter has been inserted and may be kept in the expanded state until the treatment is terminated. Also after termination of the treatment and withdrawal of the treatment catheter, the distal balloon member will preferably be kept in the expanded state or even be expanded more, to ensure closure of the puncture site.

According to a preferred embodiment, the distal balloon member in an expanded state at least partially extends beyond the distal end of the sheath. To extend beyond the distal end of the tubular body of the sheath is to be understood as extending distally from the distal end of the tubular member of the sheath. At the same time, the distal balloon member preferably also extends in a radial direction from the outer surface of the tubular body of the sheath in an expanded state. The expanded state of the distal balloon member or other balloon member will hereinafter also be referred to as inflated state. With the distal balloon member at least partially extending beyond the distal end of the tubular body of the sheath, pressure on the outside of a vessel wall, to which the distal end of the tubular body of the sheath is adjacent, is only applied if the distal balloon member is inflated or expanded. In a deflated, collapsed or unexpanded state, in contrast, no pressure is applied to the outside of the vessel wall by the distal balloon member. This is advantageous as instruments for the intervention may be guided through the sheath of the vascular closure device, in particular through the tubular body, during the intervention and a blocking of the puncture by pressure applied to the surrounding vessel wall or to the puncture itself would inhibit such guiding and advancing of instruments. Nevertheless, the distal end of the tubular body of the sheath can be brought in close vicinity or may abut to the outside of the vascular wall, when the distal balloon member is deflated. Thereby, a secure guidance of instruments through the sheath to the puncture site and into the blood vessel can be ensured. On the other hand, once the intervention is terminated and all instruments have been removed, the sealing of the puncture site can be effected by inflating the distal balloon member, which according to the preferred embodiment then in the inflated state extends beyond the distal end of the tubular body of the sheath. With treatments such as thrombolysis treatments, the catheter for delivering the treatment agent may be placed before the distal balloon member is expanded. During the subsequent treatment, the distal balloon member may already be expanded. The delivery of treatment agent is nevertheless still ensured.

According to one embodiment the at least one expandable anchor member and the at least one distal balloon member are provided on the circumferential surface of the tubular body of the sheath. By providing the members on the circumferential surface, which may also be referred to as the outside of the tubular body of the sheath, no obstacles are provided on the inner side of the tubular body and at the distal end of the inner side of the tubular body. Thereby intervention instruments or treatment catheters may be inserted into and guided through the tubular body of the sheath of the vascular closure device. Being provided on the circumferential surface according to the invention means, that the members are attached to or integrated in the outer surface of the tubular member. As already explained above, the expandable anchor member and the distal balloon member are preferably expandable at least in a radial direction of the tubular body of the sheath.

Preferably, the at least one expandable anchor member and the at least one distal balloon member are expandable separately. By allowing for a separate expansion or inflation of the two different members, the functionality of the vascular closure device can be increased. In particular, a subsequent expansion of the distal balloon member after expansion of the expandable anchor member will be possible. In that case the vascular closure device having only the anchor member expanded, may serve for example as a delivery channel or vascular sleeve for further intervention instruments such as vascular balloon catheters or the like. Once the intervention through the vascular closure device, in particular the sheath of the vascular closure device is completed, and the intervention instruments have been removed from the vascular closure device, the distal balloon member may be inflated to apply pressure to the puncture site and assist in closing the puncture site. At that point, the expandable anchor member is preferably still inflated. This will ensure holding the sheath and in particular the tubular body in the desired position. In addition, the expanded expandable anchor member provides a counter force opposite to the pressure force applied by the distal balloon member on the vascular wall. If only the application of pressure on the vascular wall is intended, the two members, that means expandable anchor member and distal balloon member may be expanded or inflated simultaneously.

In a further preferred embodiment, the at least one expandable anchor member and the at least one distal balloon member are expanded by separate expansion means. The expansion means may in particular be a fluid channel terminating in an inflation hole for a balloon member or a pulling or pushing unit for causing a mesh to expand. As according to the preferred embodiment, the members are expanded by separate expansion means, an unintended expansion of one of the members during expansion of the respective other member may reliably be avoided.

In a preferred embodiment, the at least one expandable anchor member is a balloon member. In this case the separate expansion means for the expandable anchor member and the distal balloon member may be two separate fluid channels, one for providing fluid to an inflation hole for the expandable anchor member and the other for providing fluid to an inflation hole for the distal balloon member. The fluid channels may be provided as lumen in the wall of the tubular body of the sheath. The respective inflation holes are provided in the outside of the tubular body.

According to a preferred embodiment, the vascular closure device further comprises an elongated dilator movably arranged within the sheath.

An elongated dilator according to the present invention is preferably a device for dilating the puncture in the vessel wall. The dilator has an inner lumen for at least receiving a guide wire. The dilator is made of a rigid material in order to be able to perform the dilation of the puncture. By providing a vascular closure device which includes a movably arranged dilator, the sheath of the vascular closure device can be introduced together with the dilator and thus serve as an insertion sleeve for the dilator. No additional sleeve has to be provided for the dilator. In addition, to the sheath serving as a sleeve for the dilator, the dilator on the other hand may serve as positioning means and support for the sheath during the insertion of the vascular closure device into the tissue.

The dilator is movably arranged with the sheath, so that it may be removed from the sheath after dilation of the puncture site. Therefore, the movement of the dilator in the proximal direction is not limited in the sheath. Preferably, the dilator, however, has a terminal position which it can reach in the sheath. At that terminal position no further movement of the dilator in the distal direction of the sheath is possible.

According to one embodiment, with the dilator being inserted into the sheath, the tip of the dilator in a terminal position of the dilator extends beyond the distal end of the sheath by a predefined distance.

The tip of the dilator denotes the distal end of the dilator. In the inserted state at the final position, this tip extends beyond the distal end of the sheath and in particular beyond the distal end of the tubular body by a predefined distance. At this final position, the dilator cannot be advanced further from the final position in the distal direction. By having a predefined distance of the tip of the dilator to the distal end of the sheath, the positioning of the sheath outside of the vessel wall can be ensured by the dilator. In particular, the tip of the dilator is introduced into the blood vessel through the puncture site. The dilator has a lumen which can at least receive a guide wire. Preferably, the diameter of the lumen is, however, larger than the diameter of the guide wire. Thereby, once the tip enters the blood vessel, back flow of blood through the lumen of the dilator can be observed by the physician. The blood vessel is preferably an artery and the physician will thus detect backflow of arterial blood. Once the backflow is detected, the physician does not advance the vascular closure device further. With the tip of the dilator extending beyond the distal end of the sheath, the secure positioning of the sheath outside of the blood vessel is ensured. The tip of the dilator is preferably conically shaped to facilitate advancing of the dilator over the guide wire in the tissue and entry into the vessel wall.

According to a preferred embodiment, in a distance to the distal end of the dilator the dilator has a step in the outside. The step denotes a rapid increase of the outer diameter of the dilator. The tip of the dilator is preferably shaped conically and the step is adjacent to the conical area of the tip. By providing such a step, a haptic feed back can be provided to the physician, when advancing the dilator through the tissue and into the vessel. Once the step reaches the vessel wall, a stop is signalled to the physician. As the dilator in the final position within the sheath preferably extends beyond the distal end of the sheath by a predefined distance, the position of the sheath is also known, once the step reaches the vessel wall. Preferably, the distal end of the sheath, in particular the distal end of the tubular body, is aligned with the position of the step in the dilator. This means, that once the step in the outside of the dilator reaches the vessel wall, also the distal end of the sheath and in particular the tubular body of the sheath is at the outside of the vessel wall or in immediate vicinity to the outside of the vessel wall.

According to a further embodiment, the dilator has an enlarged portion forming a rest near the proximal end of the dilator and the sheath has a seat for receiving the enlarged portion of the dilator.

By providing a rest and a seat on the dilator and the sheath, respectively, the final position of the dilator in the sheath can be secured. As the seat and rest are preferably provided near the proximal end of the dilator, insertion of the dilator into the sheath is facilitated. The seat in the sheath may be provided in a hub which is attached to or integrated with the proximal end of the tubular body of the sheath. In a distal direction the diameter of the seat decreases until it reaches the diameter of the lumen of the tubular body. As this seat is provided at the proximal area of the sheath, the insertion of the dilator by the physician is facilitated compared to advancing a dilator through a seat at the distal end of the sheath. This is in particular due to the fact that steering of the distal end of the dilator in a position further away from the physician is more difficult than at the proximal end of the vascular closure device.

The inclination of the wall of the seat and the rest preferably correspond, so that the surfaces of the seat and the rest abut in the final position of the dilator in the sheath. Once the rest and seat abut, preferably the tip of the dilator extends over the distal end of the sheath and in particular of the tubular body of the sheath. The distance by which the tip extends over the distal end of the sheath is thus preconfigured and a distance of the distal end of the sheath from the distal end of the dilator, which secures positioning of the sheath outside of the blood vessel, when the tip enters the blood vessel, can be set.

According to one embodiment, in the expanded state of the distal balloon member and the adjacent expandable anchor member, the distal balloon member and the adjacent expandable anchor member are at least partially in contact with each other.

Thereby, the distal balloon member may rest against the anchor member, while applying pressure to the vessel wall. Hence, the pressure which can be applied to the specific area at and/or around the puncture site in the vessel wall can be increased.

In a preferred embodiment, at least the at least one distal balloon member carries haemostatic agent.

Carrying haemostatic agent according to the invention, encompasses, the agent being delivered through the material of the distal balloon member, the distal balloon member being coated with the agent or the agent being incorporated into the material of the distal balloon member. In all cases, the haemostatic agent can be delivered directly to or into the close vicinity of the puncture site. Thereby, coagulation of blood at the puncture site and thus sealing of the puncture site is promoted. As the haemostatic agent is delivered by the distal balloon member which forms part of the vascular closure device, no additional device has to be inserted into the tissue.

According to a further aspect, the invention relates to a method of positioning a vascular closure device comprising a sheath having a distal end and at least one proximal end, at least partially in tissue in the vicinity of a puncture site of a vascular wall. The sheath comprises a tubular body. The method is characterized in that the method at least comprises the step of placing at least part of the tubular body of the sheath in immediate vicinity of the puncture site of the blood vessel. The tubular body of the sheath comprises at least one distal balloon member arranged at the distal end of the tubular body of the sheath and at least one expandable anchor member arranged proximal to the distal balloon member on the tubular body of the sheath, with the distal end of the tubular body of the sheath outside of the blood vessel. The method further comprises the step of expanding at least one of the expandable anchor members for fixating the sheath in the tissue.

Positioning a vascular closure device in tissue in the vicinity of a puncture site of a vascular wall according to the invention comprises advancing the vascular closure device to the desired position as well as arranging the individual parts of the vascular closure device for sealing the puncture site in the vessel wall.

The step of placing at least part of the tubular body of the sheath in immediate vicinity of the puncture site of the blood vessel comprises introducing part of the tubular body, in particular the distal area of the tubular body, through the skin into the tissue covering the vessel wall. The placing of the tubular body is preferably carried out via a guide wire which had been introduced previously. The distal area of the tubular body is introduced into the tissue and placed such that the distal end of the tubular body is in immediate vicinity of the puncture site of the blood vessel. The distal end of the tubular body of the sheath is thus placed outside of the blood vessel.

According to the invention, at least one of the expandable anchor members is expanded for fixating the sheath in the tissue. By expanding the expandable anchor member the tubular body, at which the expandable anchor member is provided, is fixated in the tissue, thereby fixating the entire vascular closure device.

By placing and positioning the sheath and in particular the tubular body of the sheath at the desired position in the tissue outside of the blood vessel and fixating the vascular closure device by expanding an expandable anchor member which is also located outside of the blood vessel, a number of advantages are achieved. In particular, as the fixation or anchoring is performed outside of the blood vessel, the anchoring means do not disturb or hinder any intervention through the puncture site and inside of the blood vessel. As the expandable anchor member is provided on a tubular member of the sheath, the intervention can be performed through the sheath, whereby the sheath serves as a vascular sleeve. Furthermore, as the expandable anchor member is arranged proximal to a distal balloon member and that in a proximal distance from the distal end of the tubular body of the sheath, occlusion of the puncture site during the intervention by the expandable anchor member does not occur and the intervention is thus not hindered. On the other side, the fixating of a vascular closure device by the expandable anchor member which is arranged proximal to a distal balloon member allows for rapid pressure application onto the puncture site after termination of the intervention. In particular, the distal balloon member is already positioned and its position is fixated by the expandable anchor member. Hence, after termination of the intervention, the distal balloon member can be expanded immediately.

According to a preferred embodiment, the vascular closure device comprises a dilator and the method comprising the step of inserting the dilator into the sheath before placing the sheath in the vicinity of the blood vessel and the step of withdrawing the dilator after expansion of the expandable anchor member.

By introducing the sheath of the vascular closure device with a dilator inserted therein, the overall treatment time can be decreased. The dilator is used for dilating the puncture site for the intervention. At the same time, with the sheath being provided on the dilator, the sheath can be positioned. Hence two treatment steps are carried out simultaneously.

By expanding the expandable anchor member, the sheath is securely fixed in the tissue, and the withdrawing of the dilator does not affect the position of the sheath. After the dilator has been withdrawn, intervention instruments such as catheters, introducers or delivery systems can be passed through the sheath.

According to a preferred embodiment, the method comprises the step of inflating the distal balloon member after expansion of the expandable anchor member.

Preferably, the distal balloon member is expanded after the intervention has been terminated and all instruments have been removed from the sheath. By inflating the distal balloon member, pressure is built up against the vessel wall and the sealing of the puncture site is improved.

According to a preferred embodiment, during the placing of the sheath in the vicinity of the blood vessel, the dilator is advanced over a guide wire into the puncture site until a step on the outside of the dilator abuts with the outside of the vascular wall.

Thereby, the correct positioning of the sheath can be monitored. The dilator has a lumen for receiving the guide wire. The lumen has a diameter greater than the diameter of the guide wire. Once the tip of the dilator passes through the puncture site, blood will flow through the lumen of the dilator. Thereby, the physician will be aware of the fact that the dilator tip has reached the inside of the blood vessel. The tip of the dilator in a final position of the dilator in the sheath preferably extends over the distal end of the tubular body of the sheath by a predetermined distance. The vascular closure device is preferably inserted into the tissue with the dilator being in this final position within the sheath. As the dilator is advanced until the dilator abuts with the outside of the vascular wall, the correct positioning of the distal end of the sheath in the vicinity of the outside of the vascular wall can be ensured.

According to one embodiment, the method comprises the steps of:

inserting a dilator having a lumen for at least a guide wire into the sheath of the vascular closure device, advancing the dilator in the sheath in a distal direction, until a final position with the tip of the dilator extending beyond the distal end of the sheath is reached, inserting the dilator with the sheath over a guide wire into the tissue, advancing the dilator and sheath until the tip of the dilator enters the blood vessel through the puncture site of the vessel wall, monitoring backflow of blood through the dilator to confirm positioning of dilator, expanding the at least one expandable anchor member, withdrawing the dilator from the sheath, and after termination of intervention, expanding the distal balloon member.

In this embodiment, the steps are carried out in the order as indicated. With this embodiment, the advantages of the present invention can be used best. In particular the insertion of the sheath at the beginning, that means before intervention, allows for using the sheath in the subsequent intervention steps. The advancing of the tip of the dilator into the blood vessel on the one hand provides dilation of the puncture site for the subsequent intervention and on the other hand indicates the position of the dilator to the physician. For this purpose, the physician monitors the backflow of blood through the dilator. In particular the physician will notice the back flow of blood and thus does not have to use contrast media to determine the position of the dilator and thereby the position of the sheath. According to one embodiment, the method comprises the method step of further advancing the dilator with the sheath until a step on the outside of the dilator abuts with the outside of the vessel wall. Advancing the dilator until a step abuts with the outside of the vessel wall, provides additional indication of the correct position of the dilator and ensures that the sheath on the dilator is positioned in the close vicinity of the vessel wall. Due to the provision of the step in the outside of the dilator further advancing is, however, not possible and thereby unintended entry of the sheath into the blood vessel is avoided. By expanding the distal balloon member after the intervention with the expandable anchor member still being expanded, application of pressure to the puncture site can be ensured thereby promoting sealing of the puncture site.

For interventions, such as thrombolysis treatments, a different sequence of steps may be performed. Thrombolysis, which is also referred to as lysis therapy or lysis, is a treatment to dissolve dangerous clots in blood vessels, improve blood flow, and prevent damage to tissues and organs. A long catheter, which is also referred to as the treatment catheter, delivers thrombolytic drugs directly to the site of the blockage. Acute limb ischaemia is one of the most severe conditions requiring a local arterial lysis therapy. In many cases the thrombolysis treatment has to be stopped due to massive bleeding especially in the groin around the puncture site.

Reasons for acute artery occlusion requiring thrombolysis are for example thrombembolic occlusion of arterial vessel, thrombotic occlusion of the native artery, thrombotic occlusion of the pretreated artery (stent) or thrombotic occlusion of bypass grafts.

According to one embodiment, the method therefore further comprises the step of expanding the distal balloon member after expansion of the expandable anchor members and after insertion of a treatment catheter for thrombolysis treatment.

The closure device of the present invention can thus be used as an add-on during current thrombolysis therapy. By using the closure device of the invention, bleeding complications can be reduced. In addition, the thrombolysis success rate can be increased. The puncture site can be protected by stabilizing the sheath. Furthermore additional features of the closure device can be used. No elements of the closure device are intravascular. After termination of the intervention, in particular, after termination of the thrombolysis, nothing is left in the body of the patient. As the closure device is also used as a guiding device for the treatment catheter during the intervention, the overall intervention steps are reduced.

According to a preferred embodiment of the thrombolysis treatment is carried out while the distal balloon member is expanded. Thereby, bleeding during the thrombolysis treatment can be avoided.

After termination of the thrombolysis treatment, the treatment catheter may be withdrawn and the distal balloon member may be further expanded to apply increased pressure on the puncture site. Thereby closure of the puncture site may be improved.

According to one embodiment, the method comprises the steps of:
inserting a dilator having a lumen for at least a guide wire into the sheath of the vascular closure device,
advancing the dilator in the sheath in a distal direction, until a final position with a tip of the dilator extending beyond the distal end of the sheath is reached,
inserting the dilator with the sheath over a guide wire into the tissue,
advancing the dilator and sheath until the tip of the dilator enters the blood vessel through the puncture site of the vessel wall,
monitoring backflow of blood through the dilator to confirm positioning of dilator
preferably further advancing the dilator with the sheath until a step on the outside of the dilator abuts with the outside of the vessel wall,
expanding the at least one expandable anchor member,
withdrawing the dilator from the sheath, inserting a treatment catheter,
expanding the distal balloon member and
initiating a thrombolysis treatment.

The thrombolysis treatment with the closure device of the present invention may comprise the following steps.

Place guide wire in femoral artery

Placement of the closure device via the wire after the punction of the femoral artery and placement of the guide wire, thus in the beginning of the thrombolysis treatment Removal of dilator, blood backflow indicates correct position Inflation of the anchor element—the inflated balloon secures the position of the closure device in the tissue Placement of the treatment catheter Inflation of distal balloon member—Start of thrombolysis therapy via catheter perfusion The closure device has a protection function—both inflated balloons protect bleeding from the tissue and the artery Removal of the treatment catheter after the end of thrombolysis therapy. The closure device performs its closure function—the balloons close the artery supporting the haemostasis process.

Removal of the closure device.

During the thrombolysis therapy the inflated balloons are tamponing damaged vessels along the puncture channel. The inflated distal balloon member is augmenting the puncture site in the artery and bleeding along the sheath is minimized. In addition, the puncture site is protected by stabilizing sheath. At the end of the therapy the closure device may be used to assist closure of the puncture site. The closure device may, however, also only be used during the therapy and may be removed after the therapy.

By combining access, protection and, if required, closure function in a single device, the closure device has the potential to significantly improve the safety and efficiency of the thrombolysis therapy.

Preferably, the method according to the invention is carried out with a vascular closure device according to the invention.

Features and advantages of the method according to the invention also apply to the vascular closure device of the invention and vice versa. Some features and advantages will thus only be described with respect to one of the aspects of the invention, but are applicable to the respective other aspect.

BRIEF DESCRIPTION OF THE DRAWINGS

The invention will hereinafter be described again with reference to the enclosed figures, wherein:

FIGS. 3 and 4 show schematic views of an embodiment of the dilator of the vascular closure device;

FIGS. 7-10 show schematic views of different steps of an embodiment of the method of positioning the vascular closure device according to the invention in tissue; and FIGS. 11-14 show schematic views of different steps of an embodiment of the method of using the vascular closure device as a thrombolysis treatment device according to the invention.

The invention is not limited to the embodiment shown in the Figures. Individual features shown in the Figures may be used in a different embodiment without necessitating the use of all features of the depicted embodiment in the different embodiment.

DETAILED DESCRIPTION OF THE PREFERRED EMBODIMENT

Figure 1:
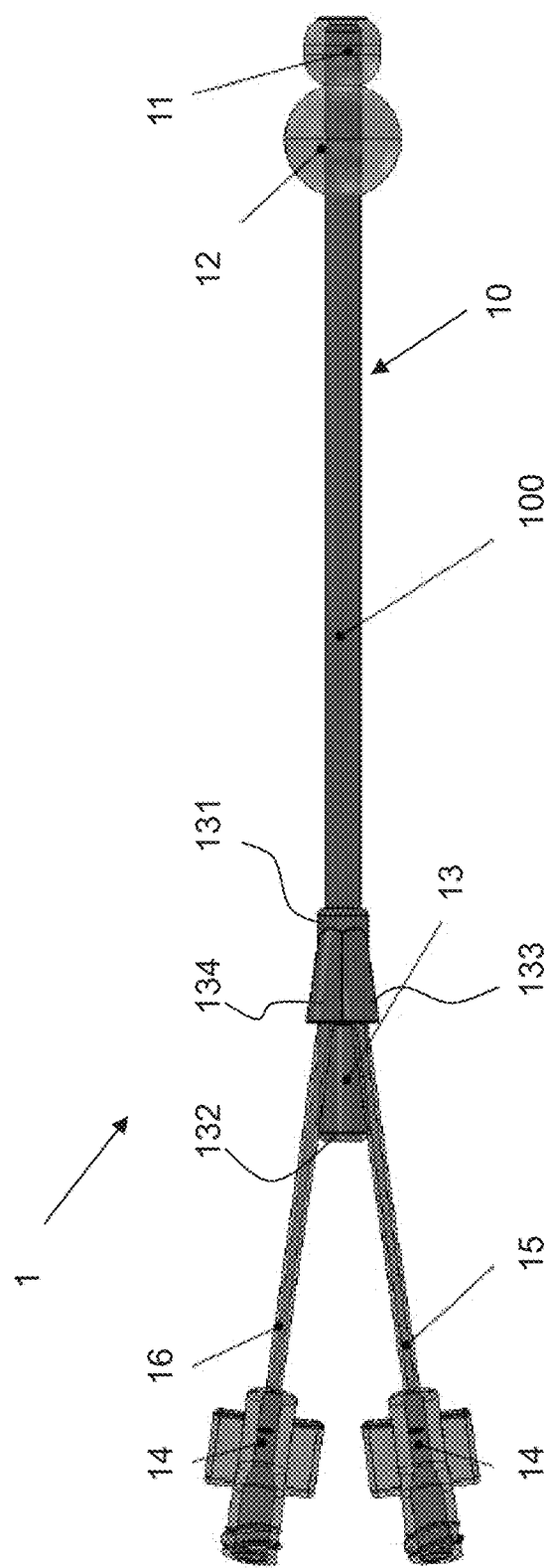
FIG. 1 shows a schematic view of an embodiment of the sheath of an embodiment of the vascular closure device.

FIG. 1 shows an embodiment of the sheath 10 of the vascular closure device 1 of the invention. The sheath 10 comprises an elongated tubular body 100. In the depicted embodiment, in the area of the distal end of the sheath 10, in particular of the elongated body 100, two expandable members 11 and 12 are provided. Member 11 is arranged at the distal end of the tubular body 100 of the sheath 10 and is a balloon member. Member 11 is therefore also referred to as distal balloon member 11. Proximally adjacent to the distal balloon member 11, an expandable anchor member 12 is arranged on the tubular body 100 of the sheath 10. In the depicted embodiment, the expandable anchor member 12 is a balloon member. The diameter of the expandable anchor member 12 which is arranged in a more proximal position than the distal balloon member 11, is larger than the diameter of the distal balloon member 11. The invention is, however, not limited to such proportions of diameters. The two members 11, 12 may also have the same diameter or the distal balloon member 11 may have a diameter larger than the diameter of the expandable anchor member 12. The two members 11, 12 are in fluid communication with two lumens (not shown) in the tubular body 100 of the sheath 10, which have inflating holes at their distal ends to provide media to the members 11, 12. The inflating holes are provided in the outside of the sheath 10 in the area of the respective members 11, 12.

At the proximal end of the tubular body 100 of the sheath 10, a hub 13 is attached to the tubular body 100. The hub 13 has four ports 131, 132, 133, 134. The distal port 131 receives the proximal end of the tubular body 100 of the sheath 10. The central proximal port 132 is aligned with the distal port 131 of the hub 13. In addition, two further proximal ports 133, 134 branch off of the hub 13. These two ports 133, 134 are used for receiving extension lines 15, 16 for the distal balloon member 11 and the expandable anchor member 12, respectively. For providing media to the expandable anchor member 12 and the distal balloon member 11, through the extension lines 15 and 16 and the elongated body portion 100 of the sheath 10, adapters 14 are attached to the proximal ends of the extension lines 15 and 16.

Figure 2:
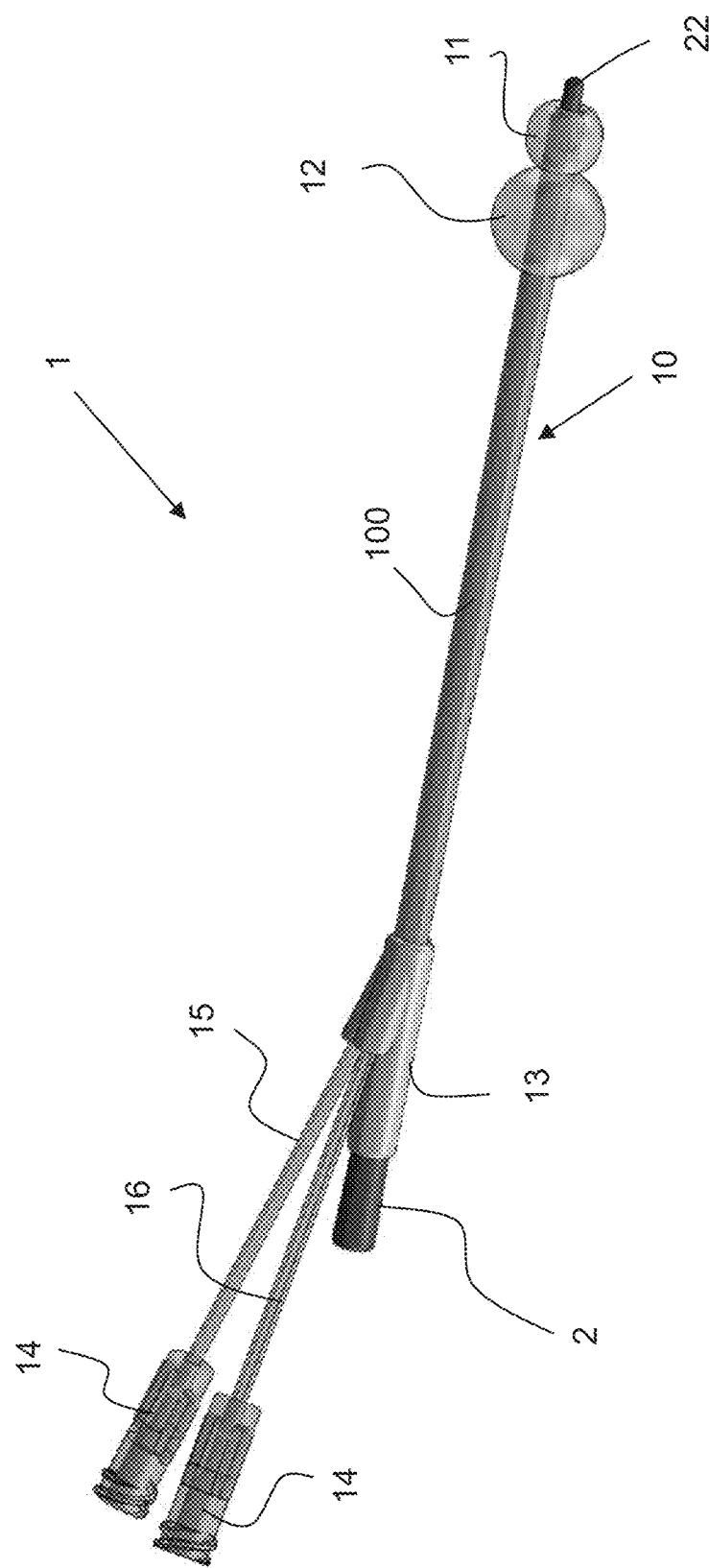
FIG. 2 shows a schematic, perspective view of the sheath of FIG. 1 with a dilator inserted therein.

FIG. 2 shows an embodiment of the vascular closure device 1 according to a preferred embodiment. In this embodiment, the sheath 10 is the embodiment of the sheath 10 as shown in FIG. 1. However, a dilator 2 is inserted into the sheath 10. In FIG. 2 only the proximal end of the dilator and the tip 22 of the dilator 2 are visible. The tip 22 extends beyond the distal end of the sheath 10, in particular of the tubular body 100. In FIGS. 1 and 2 the expandable anchor member 12 and the distal balloon member 11 are shown in an expanded or inflated state. In this state, the distal balloon member 11 extends beyond the distal end of the sheath 10 and in particular beyond the distal end of the tubular body 100 of the sheath 10. The tip 22 of the dilator 2 extends further distally than the distal area of the distal balloon member 11.

A preferred embodiment of the dilator 2 is shown in FIGS. 3 and 4 in more detail. The dilator 2 has the shape of a rod with a lumen 21 provided along its longitudinal axis. The diameter of the lumen 21 is larger than the diameter of a guide wire (not shown), which can be passed through the lumen 21. At the distal end, the dilator 2 has a tip 22, which is rounded at its most distal end and has a conical shape over the remaining part of the tip 22. The diameter of the tip 22 increased in the proximal direction. At the proximal end of the tip 22, a step 24 is formed by an abrupt increase of diameter to the diameter of the shaft 20 of the dilator 2. At the proximal end of the shaft 20 of the dilator 2, a conical rest 23 is formed by a gradual increase of diameter.

Figure 5:
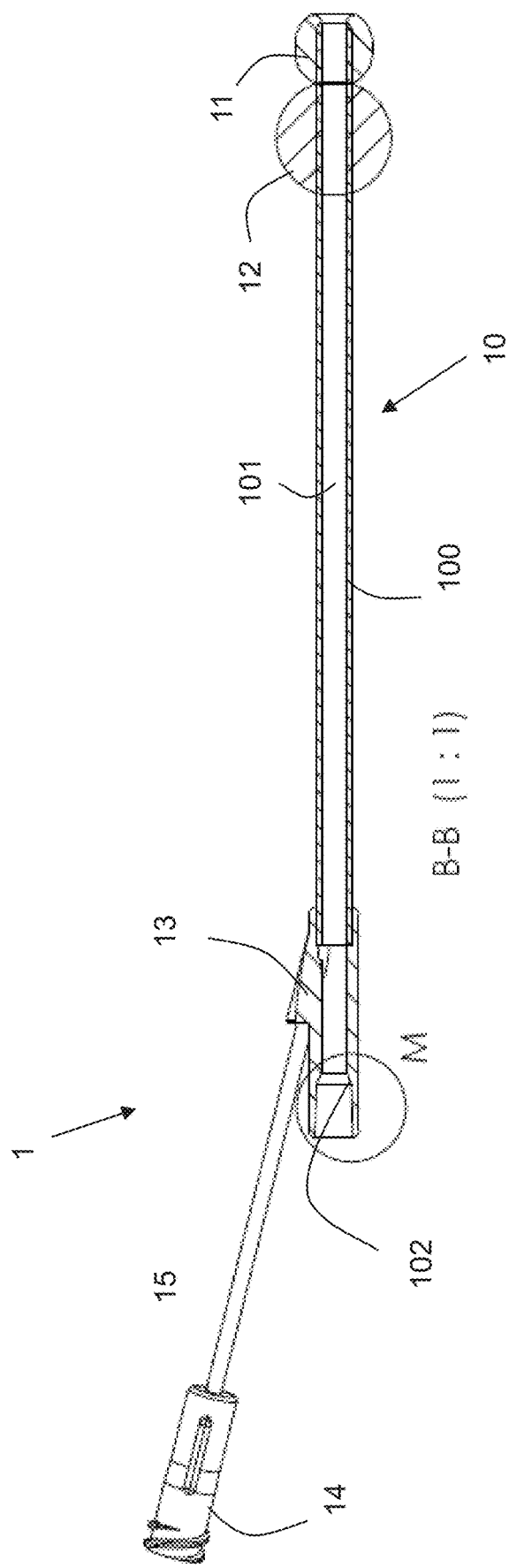
FIGS. 5 and 6 show schematic views of the embodiment of the sheath of FIG. 1.
Figure 6:
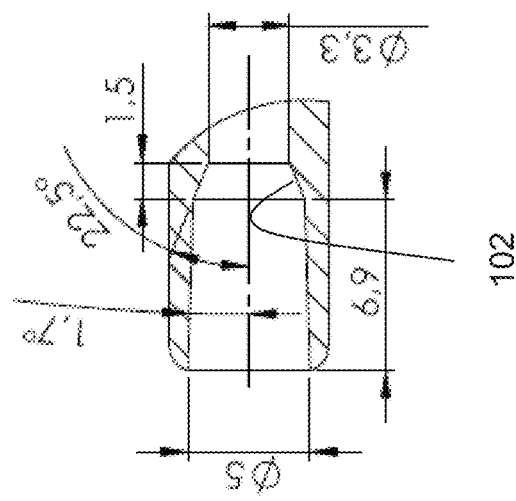

Such a dilator 2 may be introduced into a sheath 10. FIGS. 4 and 5 show the embodiment of the sheath 10 of FIGS. 1 and 2 in greater detail. As can be seen from FIG. 5, the tubular body 100 of the sheath 10 is inserted with its proximal end into a distal port 131 of the hub 13. The central proximal port 132 of the hub 13 is aligned with the distal port 131 of the hub 13. In the central proximal port 132 the diameter of the port increases towards the proximal end and thus forms a conical seat 102. This seat is also shown in FIG. 6 in greater detail.

If a dilator 2 is inserted into such a sheath 10, the tip 22 of the dilator 2 is advanced through the central proximal port 132 of the hub 13. When advanced further, the tip portion 22 and the shaft 20 of the dilator 2 pass through the distal port 131 of the hub 13 and enter the tubular body 100 of the sheath 10. The dilator 2 is advanced through the sheath 10, until the rest 23 of the dilator 2 reaches the seat 102 of the hub 13 of the sheath 10. The conical rest 23 abuts with the conical seat 102 and inhibits further advancing of the dilator 2 within the sheath 10 in the distal direction. The length of the dilator 2 is chosen such that the tip 22 of the dilator 2 extends beyond the distal end of the tubular body 100 of the sheath 10 when the rest 23 is in contact with the seat 102.

The positioning and usage of the vascular closure device 1 will now be described with reference to FIGS. 7 to 10.

For a treatment which includes an endovascular intervention, the physician will first puncture a blood vessel V by introducing a needle (not shown) through the skin, the tissue T and the vessel wall W. Thereby a puncture site P is generated in the vessel wall W. Subsequently, a guide wire G is introduced through the skin, the tissue T and the puncture site P into the vessel V. Via this guide wire, the vascular closure device 1 can now be introduced. Before the vascular closure device 1 is introduced, the dilator 2, is inserted into the sheath 10 and is advanced until the rest 23 is in contact with the seat 102. The tip 22 of the dilator 2 thus extends beyond the distal end of the tubular body 100 of the sheath 10. By pushing the dilator 2 over the guide wire G, the vascular closure device 1 will be advanced in the tissue T. The physician will move the vascular closure device 1 forward, until the tip 22 of the dilator 2 reaches the puncture site P and enters into the vessel V. As the diameter of the lumen 21 in the dilator 2 is larger than the diameter of the guide wire G, blood backflow through the lumen 21 of the dilator 2 is possible and will indicate to the physician that the tip 22 of the dilator 2 has reached the inside of the blood vessel V. The vascular closure device 1 is then further advanced thereby expanding the puncture site P in the vessel wall W. The vascular closure device 1 is advanced until the step 24 of the dilator 2 abuts with the outside of the vessel wall W. Due to the increase of diameter of the dilator 2 at the step 24, a haptic feed back is provided to the physician that the final position of the vascular closure device 1 is reached. In this position, the distal end of the tubular body 100 of the sheath 10 which corresponds to the position of the step 24, abuts with the vessel wall W or is at least in the vicinity of the vessel wall W. This situation is shown in FIG. 7.

At this stage, the physician will expand the expandable anchor member 12. In the embodiment depicted in FIG. 1, the expansion is initiated by starting media flow to the expandable anchor member 12 through the extension line 16 and a respective lumen (not shown) in the tubular body 100 of the sheath 10. Through an inflation hole (not shown) in the outside of the tubular body 100 of the sheath 10 the media reaches the inside of the expandable anchor member 12 and causes the expandable anchor member to inflate. By expanding or inflating the expandable anchor member 12, tissue T which surrounds the expandable anchor member 12 is mainly pushed in a direction perpendicular to the longitudinal axis of the vascular closure device 1. Thereby, a movement of the sheath 10 in the longitudinal direction is inhibited and the vascular closure device 1 is securely anchored to the tissue T. At this stage, which is shown in FIG. 8, the distal balloon member 11 is still in a deflated stage.

With the sheath 10 being securely fixed or anchored within the tissue T, the dilator 2 can safely be removed from the sheath 10, by pulling the dilator 2 back over the guide wire G. FIG. 9 shows the sheath 10 in the anchored position. Once the dilator 2 has been removed, intervention instruments such as catheters, introducers of delivery systems (not shown) can be advanced over the guide wire G into the vessel V, via the sheath 10 of the vascular closure device 1.

After termination of the intervention, such a balloon angioplasty, the instrument will be pulled back and removed. Also the guide wire G will be removed. At this stage, the puncture site P in the vessel wall W has to be sealed. For this purpose, the distal balloon member 11 will now be expanded. The expansion is initiated by starting media flow to the distal balloon member 11 through the extension line 15 and a respective lumen (not shown) in the tubular body 100 of the sheath 10. Through an inflation hole in the sheath 10 the media reaches the inside of the distal balloon member 11 and causes the distal balloon member 11 to inflate. As the distal end of the sheath 10 and in particular of the elongated body portion 100 had been positioned adjacent the outside of the vessel wall W, the expansion of the distal balloon member 11 will cause pressure on the outside of the vessel wall W. As shown in FIG. 10, the inflated distal balloon member 11 extends beyond the distal end of the elongated body portion 100 of the sheath 10. Thereby, the puncture site P will narrow. At this stage also haemostatic agents may be provided through the distal balloon member 11. Thereby, the healing of the puncture site P by coagulation of blood is supported.

Once the puncture site P has closed or after a predetermined period of time, the expandable anchor member 12 and the distal balloon member 11 will be deflated and the sheath 10 will be removed from the tissue T.

The closure device 1 may also serve as a treatment device for treatment of thrombolysis. In this case, the closure device 1 may be referred to as thrombolysis treatment device.

The positioning and usage of the vascular closure device 1 as treatment device for thrombolysis will now be described with reference to FIGS. 11 to 14. In this context the vascular closure device will be referred to as thrombolysis treatment device.

For the thrombolysis treatment which includes an endovascular intervention, the physician will first puncture a blood vessel V by introducing a needle (not shown) through the skin, the tissue T and the vessel wall W. Thereby a puncture site P is generated in the vessel wall W. Subsequently, a guide wire G is introduced through the skin, the tissue T and the puncture site P into the vessel V. Via this guide wire, the thrombolysis treatment device 1 can now be introduced. Before the thrombolysis treatment device 1 is introduced, the dilator 2, is inserted into the sheath 10 and is advanced until the rest 23 is in contact with the seat 102. The tip 22 of the dilator 2 thus extends beyond the distal end of the tubular body 100 of the sheath 10. By pushing the dilator 2 over the guide wire G, the thrombolysis treatment device 1 will be advanced in the tissue T. The physician will move the thrombolysis treatment device 1 forward, until the tip 22 of the dilator 2 reaches the puncture site P and enters into the vessel V. As the diameter of the lumen 21 in the dilator 2 is larger than the diameter of the guide wire G, blood backflow through the lumen 21 of the dilator 2 is possible and will indicate to the physician that the tip 22 of the dilator 2 has reached the inside of the blood vessel V. The thrombolysis treatment device 1 is then further advanced thereby expanding the puncture site P in the vessel wall W. The thrombolysis treatment device 1 is advanced until the step 24 of the dilator 2 abuts with the outside of the vessel wall W. Due to the increase of diameter of the dilator 2 at the step 24, a haptic feed back is provided to the physician that the final position of the thrombolysis treatment device 1 is reached. In this position, the distal end of the tubular body 100 of the sheath 10 which corresponds to the position of the step 24, abuts with the vessel wall W or is at least in the vicinity of the vessel wall W. This situation is shown in FIG. 11.

At this stage, the physician will expand the expandable anchor member 12. In the embodiment depicted in FIG. 1, the expansion is initiated by starting media flow to the expandable anchor member 12 through the extension line 16 and a respective lumen (not shown) in the tubular body 100 of the sheath 10. Through an inflation hole (not shown) in the outside of the tubular body 100 of the sheath 10 the media reaches the inside of the expandable anchor member 12 and causes the expandable anchor member to inflate. By expanding or inflating the expandable anchor member 12, tissue T which surrounds the expandable anchor member 12 is mainly pushed in a direction perpendicular to the longitudinal axis of the thrombolysis treatment device 1. Thereby, a movement of the sheath 10 in the longitudinal direction is inhibited and the thrombolysis treatment device 1 is securely anchored to the tissue T. At this stage, which is shown in FIG. 12, the distal balloon member 11 is still in a deflated stage.

With the sheath 10 being securely fixed or anchored within the tissue T, the dilator 2 can safely be removed from the sheath 10, by pulling the dilator 2 back over the guide wire G. FIG. 13 shows the sheath 10 in the anchored position. Once the dilator 2 has been removed, treatment instruments, in particular a treatment catheter 3 which may also be referred to as treatment sheath 3 will advanced over the guide wire G into the vessel V, via the sheath 10 of the vascular closure device 1.

In FIG. 13, the distal end of the treatment catheter 3 or treatment sheath 3 is shown in the vicinity of the puncture site P. It is well understood that the distal end of the treatment catheter 3 may also be further spaced apart from the puncture site P and the distal section of the treatment catheter 3 may be bent to extend along the vessel V. The treatment catheter 3 may be advanced to the treatment site within the vessel V.

Once the treatment catheter 3 is placed and the distal balloon member 11 will be expanded as shown in FIG. 14. The expansion is initiated by starting media flow to the distal balloon member 11 through the extension line 15 and a respective lumen (not shown) in the tubular body 100 of the sheath 10. Through an inflation hole in the sheath 10 the media reaches the inside of the distal balloon member 11 and causes the distal balloon member 11 to inflate. As the distal end of the sheath 10 and in particular of the elongated body portion 100 had been positioned adjacent the outside of the vessel wall W, the expansion of the distal balloon member 11 will cause pressure on the outside of the vessel wall W. As shown in FIG. 14, the inflated distal balloon member 11 extends beyond the distal end of the elongated body portion 100 of the sheath 10. Thereby, the puncture site P will narrow.

At this point the thrombolysis treatment starts. The treatment is carried out via catheter perfusion by means of the treatment catheter 3.

After termination of the thrombolysis treatment, the treatment catheter 3 may be removed while the distal balloon member 11 and the anchor balloon member 12 are still inflated. Also the guide wire G will be removed. In this case, the thrombolysis treatment device 1 may serve as a vascular closure device 1 as described above. Once the puncture site P has closed or after a predetermined period of time, the expandable anchor member 12 and the distal balloon member 11 will be deflated and the sheath 10 will be removed from the tissue T.

Alternatively, the anchor balloon member 12 and the distal balloon member 11 may be deflated before the treatment catheter 3 is removed. In that case, the treatment catheter 3 may be removed together with the thrombolysis treatment device 1 after termination of the thrombolysis treatment.

In one embodiment, the deflation of at least the distal balloon member 11 is performed by slowly reducing the pressure in the distal balloon member 11. Instead of completely removing the media and thereby the pressure from the distal balloon member 11, a slow reduction of media and thus the pressure in the distal balloon member 11 will result in several deflation stages of the distal balloon member 11. Thereby, the deflation of the distal balloon member 11 can be performed in such a way to allow for the surrounding tissue T to retract.

The present invention has several advantages. In particular, no parts of the vascular closure device have to remain in the body. The sheath of the vascular closure device and thus also the expandable anchor member and the distal balloon member are only provided extravascular. As the vascular closure device according to the invention serves as a guiding tube or sleeve for instruments used in the intervention, it may be placed at the beginning of the procedure and no additional placement of a separate device at the end of the intervention is necessary. In addition, the expandable anchor member fixes the position of the sheath during the intervention as well as during the sealing/healing phase. Furthermore, the placement close to the blood vessel wall, in particular the artery wall, is confirmed directly by back flow of blood, in particular arterial blood, through the dilator. In addition, after removal of the dilator, the extravascular position of the sheath is confirmed by lack of back flow of blood, in particular arterial blood through the sheath. Hence, no contrast media is necessary for the correct positioning of the vascular closure device.

What is claimed is:

1. A vascular closure device for sealing a puncture site in a vascular wall, the vascular closure device comprising:
    a sheath (10) having a distal end and at least one proximal end, wherein the sheath (10) comprises a tubular body (100) having a diameter, wherein the diameter of the tubular body of the sheath is configured to be larger than the puncture, wherein a distal balloon member (11) is firmly arranged at the distal end of the tubular body (100) of the sheath (10) and an expandable anchor member (12) is firmly arranged proximal to the distal balloon member (11) on the tubular body of the sheath (10), wherein at least the distal side of the distal balloon member (11) is a pressure area for applying pressure on the outside of the vascular wall for sealing the puncture site, and further wherein when the distal balloon member (11) and the expandable anchor member (12) are expanded, the distal balloon member (11) and the expandable anchor member (12) are at least partially in contact with each other; and
    a thrombolysis treatment catheter (3) having a distal end and a proximal end, wherein the distal end of the tubular body (100) of the sheath is open for advancing the distal end of the thrombolysis treatment catheter therethrough, wherein the thrombolysis treatment catheter is provided in the lumen of the tubular body which is surrounded by the distal balloon member and further wherein the distal end of the thrombolysis treatment catheter (3) is configured to be disposed distal to the distal end of the distal balloon member (11) when the distal balloon member (11) is expanded.

2. The vascular closure device according to claim 1, wherein the distal balloon member (11) at least partially extends beyond the distal end of the tubular body (100) of the sheath (10) when the distal balloon member (11) is expanded.

3. The vascular closure device according to claim 1, wherein the expandable anchor member (12) and the distal balloon member (11) are provided on the circumferential surface of the tubular body (100) of the sheath (10) and are expandable at least in a radial direction of the tubular body (100) of the sheath (10).

4. The vascular closure device according to claim 1, wherein the expandable anchor member (12) and the distal balloon member (11) are expandable separately by separate expansion means.

5. The vascular closure device according to claim 1, wherein the vascular closure device further comprises an elongated dilator (2) configured to be movably arranged within the sheath (10).

6. The vascular closure device according to claim 5, wherein when the dilator (2) is inserted into the sheath (10), a tip (22) of the dilator (2) in a terminal position extends beyond the distal end of the sheath (10) by a predefined distance.

7. The vascular closure device according to claim 5, wherein the dilator (2) has an enlarged portion forming a rest (23) near the proximal end of the dilator (2) and the vascular closure device (1) has a seat (102) for receiving the enlarged portion of the dilator (2).

8. The vascular closure device according to claim 7, wherein the sheath comprises a hub (13), and further wherein the seat (102) is provided in the hub (13).

9. The vascular closure device according to claim 5, wherein a step (24) is provided on the dilator (2) at a distance spaced from the distal end of the dilator (2).

10. The vascular closure device according to claim 1, wherein the expandable anchor member (12) is a balloon member.

11. The vascular closure device according to claim 1, wherein the distal balloon member (11) carries a haemostatic agent.

12. A method of positioning a vascular closure device for a thrombolysis treatment, the vascular closure device comprising a sheath (10) having a distal end and at least one proximal end, wherein the sheath (10) comprises a tubular body (100) configured to be at least partially disposed adjacent to a puncture site of a vascular wall (W) of a blood vessel (V), the method comprising:

placing at least part of the tubular body (100) of the sheath (10) having a distal balloon member (11) firmly arranged on the distal end of the tubular body (100) of the sheath (10), and an expandable anchor member (12) firmly arranged on the same tubular body (100) of the sheath (10) proximal to the distal balloon member (11), adjacent to the puncture site (P), with the distal end of the tubular body (100) of the sheath (10), the distal balloon member (11) and the expandable anchor member (12) disposed outside of the blood vessel (V) adjacent to the puncture site (P), such that when the distal balloon member is expanded, the distal balloon member contacts the outside of the vascular wall (W) of the blood vessel (V), expanding the expandable anchor member (12) for fixating the sheath (10) in the tissue (T), inserting a treatment catheter for thrombolysis treatment into the sheath, expanding the distal balloon member (11) after expansion of the expandable anchor member (12) and after insertion of the treatment catheter for thrombolysis treatment to apply pressure on the outside of the vascular wall (W) of the blood vessel (V), and delivering a thrombolytic drug through the treatment catheter directly to a site of blockage in the blood vessel (V) in order to dissolve clots in the blood vessel (V) and improve blood flow.

13. The method according to claim 12, wherein the vascular closure device (1) further comprises a dilator (2), and the method further comprises inserting the dilator (2) into the sheath (10) before placing the sheath (10) adjacent to the blood vessel, and withdrawing the dilator (2) after expansion of the expandable anchor member (12).

14. The method according to claim 13, wherein during the placing of the sheath (10) with the dilator (2) adjacent to the blood vessel, the dilator (2) is advanced over a guide wire into the puncture site until a step (24) on the outside of the dilator (2) abuts with the outside of the vascular wall.

15. The method according to claim 12, wherein the method further comprises the steps of:

inserting a dilator (2) having a lumen (21) for at least a guide wire (G) into the sheath (10) of the vascular closure device (1), advancing the dilator (2) in the sheath (10) in a distal direction, until a final position with a tip (22) of the dilator (2) extending beyond the distal end of the sheath (10) is reached, inserting the dilator (2) with the sheath (10) over a guide wire (G) into the tissue (T), advancing the dilator (2) and sheath (10) until the tip (22) of the dilator (2) enters the blood vessel (V) through the puncture site (P) of the vessel wall (W), monitoring backflow of blood through the dilator (2) to confirm positioning of the dilator (2), further advancing the dilator (2) with the sheath (10) until a step (24) on the outside of the dilator (2) abuts with the outside of the vessel wall (W), withdrawing the dilator (2) from the sheath (10) after expanding the expandable anchor member (12), and after termination of intervention, further expanding the distal balloon member (11).

16. The method according to claim 12, wherein thrombolysis treatment is carried out while the distal balloon member (11) is expanded.

17. The method according to claim 12, wherein the method further comprises the steps of:

inserting a dilator (2) having a lumen (21) for at least a guide wire (G) into the sheath (10) of the vascular closure device (1), advancing the dilator (2) in the sheath (10) in a distal direction, until a final position with a tip (22) of the dilator (2) extending beyond the distal end of the sheath (10) is reached, inserting the dilator (2) with the sheath (10) over a guide wire (G) into the tissue (T), advancing the dilator (2) and sheath (10) until the tip (22) of the dilator (2) enters the blood vessel (V) through the puncture site (P) of the vessel wall (W), monitoring backflow of blood through the dilator (2) to confirm positioning of the dilator (2), further advancing the dilator (2) with the sheath (10) until a step (24) on the outside of the dilator (2) abuts with the outside of the vessel wall (W), and withdrawing the dilator (2) from the sheath (10) after expanding the expandable anchor member (12).

18. The method according to claim 12, wherein at least the distal side of the distal balloon member (11) of the vascular closure device (1) is a pressure area for applying pressure on the outside of the vascular wall.

19. The method according to claim 12 further comprising after termination of the thrombolysis treatment, withdrawing the treatment catheter and sealing the puncture site by at least one of (i) maintaining the distal balloon member (11) in an expanded state, and (ii) further expanding the distal balloon member (11) to apply increased pressure on the puncture site.

20. A method of positioning a vascular closure device for a thrombolysis treatment, the vascular closure device comprising a sheath having a distal end and at least one proximal end, wherein the sheath comprises a tubular body, wherein a distal balloon member is firmly arranged on the distal end of the tubular body of the sheath and an expandable anchor member is firmly arranged on the same tubular body of the sheath proximal to the distal balloon member, wherein the vascular closure device is configured to be at least partially disposed in tissue adjacent to a puncture site of a vascular wall of a blood vessel, the method comprising:

placing at least the distal end of the tubular body of the sheath outside of the blood vessel adjacent to the puncture site, such that when the distal balloon member is expanded, the distal balloon member contacts the outside of the vascular wall of the blood vessel;

expanding of the expandable anchor member so as to fixate the sheath in the tissue;

inserting a treatment catheter for thrombolysis treatment into the sheath;

expanding the distal balloon member to apply pressure on the outside of the vascular wall of the blood vessel, wherein the distal balloon member is expanded after expansion of the expandable anchor member and after insertion of the treatment catheter for thrombolysis treatment into the sheath; and delivering a thrombolytic drug through the treatment catheter directly to a site of blockage in the blood vessel in order to dissolve clots in the blood vessel and improve blood flow.

21. The method according to claim 20 further comprising after termination of the thrombolysis treatment, withdrawing the treatment catheter and sealing the puncture site by at least one of (i) maintaining the distal balloon member in an expanded state, and (ii) further expanding the distal balloon member to apply increased pressure on the puncture site.

* * * * *